United States Patent [19]

Weiss et al.

[11] Patent Number: 5,708,182

[45] Date of Patent: Jan. 13, 1998

[54] METHOD FOR PREPARATION OF 2-IMINO 4-OXO-5-PHENYLOXAZOLIDINE

[75] Inventors: Stefan Weiss, Trostberg; Martina Lobensommer, Tacherting, both of Germany

[73] Assignee: SKW Trostberg Aktiengesellschaft, Trostberg, Germany

[21] Appl. No.: 627,951

[22] Filed: Apr. 3, 1996

[30] Foreign Application Priority Data

May 30, 1995 [DE] Germany .................. 195 20 111.6

[51] Int. Cl.⁶ .................................................. C07D 263/40
[52] U.S. Cl. ........................................................... 548/225
[58] Field of Search ................................................ 548/225

[56] References Cited

U.S. PATENT DOCUMENTS 2,892,753  6/1959  Schmidt .................... 548/225
3,029,189  4/1962  Hardy ....................... 548/225
3,321,470  5/1967  Howell ..................... 548/225

*Primary Examiner*—Robert Gerstl
*Attorney, Agent, or Firm*—Kenneth P. Glynn, Esq.

[57] ABSTRACT

A process for the preparation of 2-imino-4-oxo-5-phenyloxazolidine, which is used in medical applications under the name of pemolin, is described. The preparation proceeds by reacting at 10° to 150° C., optionally in the presence of a base catalyst, an aliphatic or an aromatic mandelic acid ester with an alkali or alkaline earth metal hydrogencyanamide, which can be prepared in situ; followed by treating the obtained reaction mixture or the metal salt isolated therefrom with a protonic acid, at temperatures from −30° to 150° C. until a pH value from 2 to 10 is reached.

19 Claims, No Drawings

METHOD FOR PREPARATION OF 2-IMINO 4-OXO-5-PHENYLOXAZOLIDINE

BACKGROUND OF THE INVENTION

1. Field of the Invention

The present invention is directed to a process for preparing 2-imino-4-oxo-5-phenyloxazolidine. It involves reaction of an aliphatic or aromatic mandelic acid ester with an alkali metal or alkaline earth metal hydrogencyanamide with subsequent treatment with a protonic acid.

SUMMARY OF THE INVENTION

A process for the preparation of 2-imino-4-oxo-5-phenyloxazolidine, which is used in medical applications under the name of pemolin, is described.

The preparation proceeds by reacting at 10° to 150° C., optionally in the presence of a base catalyst, an aliphatic or an aromatic mandelic acid ester with an alkali or alkaline earth metal hydrogencyanamide, which can be prepared in situ; followed by treating the obtained reaction mixture or the metal salt isolated therefrom with a protonic acid, at temperatures from −30° to 150° C. until a pH value from 2 to 10 is reached.

DETAILED DESCRIPTION OF THE PRESENT INVENTION

The present invention describes a process for the preparation of 2-imino-4-oxo-5-phenyloxazolidine of the formula

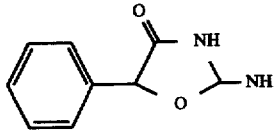

or of its tautomeric forms such as, for example, 2-imino-5-phenyl-4(5H)-oxazolone. This compound and its tautomers which are known under the name of Pemolin, are useful medical agents.

The preparation of Pemolin via the reaction of mandelic acid ethyl easter with free guanidine base is known, see U.S. Pat. No. 2,892,753. A similar preparative method was also described by A. Kleemann and J. Engel in "Pharmaceutical Material", p. 363, Georg Thieme Publishers, Stuttgart, 1978.

A drawback of this method is the fact that the free guanidine base is not very stable; and that in the reaction with the mandelic acid ester gaseous ammonia is liberated in equimolar amounts as the by-product. Moreover, upon heating of the free guanidine base there are formed several nitrogen-containing open-chain or heterocyclic products.

It was, therefore, of interest to develop a preparative method which would not show the above drawbacks, and which would allow a relatively facile route to Pemolin without the necessity of isolating possible intermediates.

The object was solved by a process for the preparation of 2-imino-4-oxo-5-phenyloxazolidine of the formula

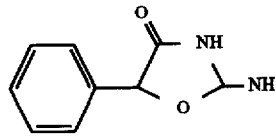

and/or its tautomeric forms, wherein a mandelic acid ester is reacted with an alkali or alkaline earth metal hydogencyanamide in a molar ratio of 1:2 to 1:0.5, preferably 1:1.25 to 1:1, at temperatures in the range of 10° to 150° C.; and wherein the obtained reaction mixture or the metal salt isolated therefrom are thereafter acidified to a pH value of 2 to 10, preferably of 3 to 6, at temperatures from −30° to 150° C., preferably from 10° to 80° C.

It is known that alcohols react with cyanamid only under very acidic conditions at pH values below zero; in the above described process it was possible, however, to accomplish the addition of the hydroxyl group of the mandelic acid ester to the nitrile group of the hydrogencyanamide at pH values corresponding to a lightly acidic or even basic pH range. This was astonishing and totally unexpected.

According to the invention, the reaction takes place in water and/or an organic solvent. An alcohol having 1 to 4 carbon atoms is preferred.

The reaction of the mandelic acid ester with the hydrogencyanamid salt is conducted in the temperature range from 10° to 150° C.; the boiling temperatures of the above mentioned $C_{1-4}$ alcohols are, therefore, particularly advantageous.

The reaction time varies from 1 to 20 hours, depending on the reaction temperature. In a preferred embodiment of the process of this invention, the reaction mixture is heated at reflux for 6 to 12 hours.

The mandelic acid ester and the alkali or alkaline earth metal hydrogencyanamide are used in a molar ratio of 0.5 to 2.0, with molar ratios of 0.8 to 1.0 being preferred.

In another preferred embodiment of the present process, the reaction can be performed in the presence of an added base catalyst. This variant is particularly recommended when the mandelic acid ester and the hydrogencyanamide salt are employed in equimolar amounts; or if an excess of the mandelic acid ester is used.

Useful catalysts are alkoxides or hydroxides of alkali or alkaline earth metals. However, even their phenoxides can be used as the base catalysts. Another advantage of the process of the invention is that excess of the hydrogencyanamide salt also functions as the base catalyst. The aforementioned catalysts are used in molar ratios of 1:0.25 to 1:0.5.

Generally, the mandelic acid esters are aliphatic $C_{1-10}$ esters, preferably methyl or ethyl esters; or phenyl or benzyl esters of DL-, D(−)- or L(+)-mandelic acid. By the term hydrogencyanamide salts are meant alkali or alkaline earth hydrogencyanamides, with sodium hydrogencyanamide (monosodium cyanamide) being preferred.

The hydrogencyanamide salt can also be prepared in a very simple manner by the reaction of an alkoxide or a hydroxide of an alkali or alkaline earth metal with cyanamide; the produced intermediate can be reacted directly without isolation with the mandelic acid ester. In a preferred embodiment of the invention, one reacts anhydrous crystalline cyanamid (cyanamid SKW F 1000) with a 30% solution of sodium methoxide in methanol in either equimolar amounts, or in a molar ratio of 1:1.25 at 10° to 30° C.

According to the invention, the cyanamide and the alkoxide are used in molar ratios of 1:1.25 to 1:1.5, when sodium hydrogencyanamide and the mandelic acid ester are reacted in equimolar amounts. Solid cyanamide (cyanamid SKW F 1000) as well as sodium hydrogencyanamide are known commercially available products.

The product obtained by the reaction of the mandelic acid ester with the hydrogencyanamide salt is acidified using a mineral or organic acid to a pH value of 2 to 10; the preferred pH range is 3 to 6. The addition of acid takes place at temperatures of −30° to 150° C., preferably at 10° to 80° C.; the time of the addition is from 5 minutes to 5 hours.

After acidification which is preferably accomplished using hydrochloric or acetic acid, the formation of pemolin is completed by additional stirring of the reaction mixture at temperatures of 10° to 150° C., preferably of 20° to 80° C. The reaction time after acidification depends upon the temperature and may be as long as 15 hours; as a minimum, 30 minutes were shown to be sufficient.

According to the present invention one can also operate by filtering the reaction mixture prior to acidification and isolating the sodium salt of pemolin. In a subsequent step, the sodium salt of pemolin is then transformed into free pemolin.

The remaining isolation steps proceed in a known manner. The reaction mixture is filtered and washed with water until salt-free. As an additional purification step, one may also heat the product in distilled water or with an alkoxide.

The advantages of the process of the present invention are illustrated in the examples that follow.

EXAMPLES

Example 1

To a mixture of 100 gms of methanol and 180 gms (1 mole) of a 30% methanolic solution of sodium methoxide, are added with vigorous stirring 42.1 gms (1 mole) of 99.8% crystalline cyanamide (cyanamide SKW F 1000) while maintaining the temperature inside the flask at 15° to 20° C. Stirring was continued for an addition hour at 15° C. Then, 125 gms (0.75 mole) of the methyl ester of DL-mandelic acid were added and the reaction mixture was stirred at reflux for 12 hours. The mixture was then cooled to 15° C. and concentrated hydrochloric acid was slowly added with external cooling until a pH value of 5.5 was reached (20° C). The reaction mixture was stirred under reflux for another 8 hours. After cooling to 15° C., the residue was isolated by suction and washed with distilled water until chloride-free and then 3 times with 100 ml methanol portions each time. Drying in vacuum at 80° C./20 mbars yielded 109.4 gms (82.8%) of product, cappilary melting point (decomp.) 252° C. The product was identified as pemolin, using mass spectrometry (M⁺=176).

Example 2

To a suspension of 64 gms (1 mole) of sodium hydrogencyanamide (monosodium cyanamide) in 250 gms of anhydrous ethanol were added with stirring at 20° C., 180.2 gms (1 mole) of ethyl ester of DL-mandelic acid. Thereafter, the mixture was heated at reflux for 12 hours. It was then cooled to 15° C., the residue was separated by suction and washed with 200 ml of ethanol. The residue (sodium salt of pemolin) was added to 500 gms of distilled water with stirring. The pH value was then brought to 5 by adding 20% hydrochloric acid with external cooling (20° C.), and the mixture was further heated at reflux (80° C.) for 6 hours. The residue was isolated by suction after cooling to 15° C., washed until chloride-free with water and dried (80° C./15 mbars). The yield of pemolin was 144 gms (81.7%), cappilary melting point 254° C. (decomp.).

Example 3

To a mixture of 100 gms of methanol of 236 gms (1.31 mole) of a 30% methanolic solution of sodium methoxide were added under vigorous stirring at an internal temperature of 15° to 20° C., 42.1 gms (1 mole) of 99.8% crystalline cyanamide (cyanamide SKW F 1000). Stirring at 15° C. was continued for 1 hour. Thereafter, 166.2 gms (1 mole) of methyl ester of DL-mandelic acid were added and the mixture was heated at reflux for 8 hours. It was then cooled to 15° C. and acidified with external cooling (20° C.) via slow addition of concentrated hydrochloric acid to a pH value of 4.5. Stirring at 20° C. was continued for 1 hour. The residue was isolated by suction, washed with distilled water until chloride-free and then three times with methanol portions of 100 ml. each time. After drying in vacuum (80° C./20 mbars) 145 gms (82.3%) of product having a cappilary melting point of 254° C. (decomp) were obtained.

Example 4

To a mixture of 150 gms of methanol and 180 gms of a 30% solution of sodium methoxide in methanol (1 mole) were added under vigorous stirring, at an internal temperature of 15° to 20° C. 42.1 gms (1 mole) of 99.8% crystalline cyanamid (cyanamide SKW F 1000). Stirring at 15° C. was continued for 1 hour. Thereafter, 166.2 gms (1 mole) of methyl ester of DL-mandelic acid were added and the reaction mixture was refluxed for 10 hours. It was cooled to 15° C. and acidified with external cooling (20° C.) by slow addition of concentrated hydrochloric acid until a pH value of 4.2 was reached. After addition of 250 ml. methanol, the reaction mixture was stirred for another two hours at 20° C. The residue was isolated by suction, washed with water until chloride-free and then 3 times with 100 ml portions of methanol each time. Drying (80° C./20 mbars) yielded 156 gms (88.5%) of product with a cappilary melting point of 256° C. (decomp.).

Example 5

To a mixture of 150 gms of methanol and 180 gms (1 mole) of 30% methanolic solution of sodium methoxide were added under vigorous stirring, at an internal temperature of 15° to 20° C., 42.1 gms (1 mole) of 99.8% crystalline cyanamide (cynamid SKW F 1000). Stirring at 15° C. was continued for 1 hour. Thereafter, 166.2 gms (1 mole) of methyl ester of DL-mandelic acid were added and the reaction mixture was refluxed for 10 hours. It was cooled to 15° C. and acidified with external cooling (20° C.) by slow addition of concentrated hydrochloric acid until a pH value of 4.2 was reached. After adding 400 ml of methanol, the mixture was refluxed for 3 hours. 250 ml of water were added and refluxing was continued for another 8 hours. The reaction mixture was then cooled to 20° C. and worked-up as in example Yield: 138 gms (78.3%) of pure, white pemolin having a melting point of 247° C.

What is claimed is:

1. Process for the preparation of 2-imino-4-oxo-5-phenyloxazolidine of the formula:

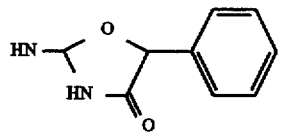

and/or its tautomeric forms, characterized in that a mandelic acid ester is treated with an alkali or alkaline earth metal hydrogencyanamide in a molar ratio of 1:2 to 1:0.5, at temperatures in the range of 10° to 150° C.; and in that thereafter the obtained reaction mixture metal salt is acidified to a PH value of 2 to 10, at temperatures from −30° to 150° C.

2. The process of claim 1 characterized in that molar ration is 1:1.25 to 1:1.

3. The process of claim 1 characterized in that reaction mixture metal salt is acidified to a PH value of 3 to 6.

4. The process of claim 1 characterized in that metal salt is acidified at temperatures from 10° to 80° C.

5. The process of claim 1, characterized in that the mandelic acid esters are aliphatic $C_1$ to $C_{10}$ esters, or phenyl or benzyl esters of DL-, D(−)- or L(+)-mandelic acid.

6. The process of claim 5 characterized in that esters are selected from the group consisting of methyl esters and ethyl esters.

7. The process of claim 5, characterized in that the hydrogencyanamid salt is sodium hydrogencyanamide.

8. The process of claim 5 characterized in that the reaction is preformed in water and/or an organic solvent.

9. The process of claim 5 characterized in that reaction is performed in an alcohol having 1 to 4 carbon atoms.

10. The process of claim 8 characterized in that the intermediate hydrogencyanamide salt is produced via the reaction of cyanamid with an alkoxide or hydroxide of an alkali or alkaline earth metal.

11. The process of claim 10 characterized in that the hydrogencyanamid salt is produced using a 30% methanolic solution of sodium methoxide with a molar ratio of cyanamide to sodium methoxide of 1:1 to 1:1.25.

12. The process of claim 11 characterized in that a base catalyst is added in a mole ratio of 1:0.1 to 1:1 based on the mandelic acid ester.

13. The process of claim 12 characterized in that a base catalyst is added in a mole ratio of 1:0.25 to 1:0.5.

14. The process of claim 12 characterized in that the base catalyst is an alkoxide, hydroxide or phenoxide of an alkali or alkaline earth metal.

15. The process of claim 14 characterized in that hydrochloric or acetic acids are used for the acidification.

16. The process of claim 15 characterized in that the obtained reaction mixture is filtered, the metal salt of pemolin is isolated and thereafter transformed into free pemolin via acidification.

17. The process of claim 15 characterized in that the acidified reaction mixture is stirred up to 15 hours in the temperature range of 10° to 150° C. preferably 20° to 80° C.

18. The process of claim 17 characterized in that the reaction product is washed with water until salt-free.

19. The process of claim 18 characterized in that the reaction product is purified via reflux using water or an alcohol having 1 to 4 carbon atoms.

* * * * *